US00PP37783P3

(12) United States Plant Patent
Bull

(10) Patent No.: US PP37,783 P3
(45) Date of Patent: Oct. 13, 2026

(54) ***ECHINACEA* PLANT NAMED 'BULLECHIPUR 121'**

(50) Latin Name: *Echinacea purpurea*
Varietal Denomination: BullEchipur 121

(71) Applicant: Hartwig Bull, Gönnebek (DE)

(72) Inventor: Hartwig Bull, Gönnebek (DE)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 19/235,215

(22) Filed: Jun. 11, 2025

(65) Prior Publication Data

US 2025/0386752 P1 Dec. 18, 2025

Related U.S. Application Data

(60) Provisional application No. 63/731,837, filed on Jun. 12, 2024.

(51) Int. Cl.
*A01H 5/02* (2018.01)
*A01H 5/12* (2018.01)
*A01H 6/14* (2018.01)

(52) U.S. Cl.
USPC ..... Plt./428
CPC ..... *A01H 6/1448* (2018.05); *A01H 5/02* (2013.01); *A01H 5/12* (2013.01)

(58) Field of Classification Search
USPC ..... Plt./428
CPC ..... A01H 5/02; A01H 5/00; A01H 6/1448; A01H 6/14
See application file for complete search history.

(56) References Cited

U.S. PATENT DOCUMENTS

| | | | | |
|---|---|---|---|---|
| 7,982,110 | B2 * | 7/2011 | Ren | A01H 5/12 800/300 |
| PP31,064 | P2 * | 11/2019 | Ren | A01H 5/02 Plt./428 |
| PP35,164 | P2 | 5/2023 | Ren | |
| PP35,286 | P3 | 7/2023 | Bull | |

OTHER PUBLICATIONS

ThinkPlants Catalog 2024-25 retrieved on Sep. 4, 2025 at https://online.flippingbook.com/view/530070179/34/, cover page, 2, 34-35, 88-89. (Year: 2025).*

Wist et al. Floral Structure and Dynamics of Nectar Production in *Echinacea pallida* var. *anugustifolia* (*Asteraceae*), Int. J. Plant Sci. 169(6):708-722, 2008. (Year: 2008).*

Greenhouse Management Supplement 2024 New Perennial Varieties retrieved on Mar. 31, 2026 at https://giecdn.blob.core.windows.net/fileuploads/upload/2024/07/01/newperennials_2024.pdf, cover page, pp. 1-23, back cover page, 14 pp. total. (Year: 2024).*

Brookgreen Gardens *Echinacea purpurea* 'PAS702918', retrieved on Aug. 27, 2025 at https://www.brookgreen.ord/plantcollection/name/echinacea-purpurea-pas702918-powwow%25C2%25AE-white, 3 pages.

* cited by examiner

*Primary Examiner* — June Hwu
(74) *Attorney, Agent, or Firm* — The Webb Law Firm

(57) ABSTRACT

A new and distinct variety of *Echinacea* plant named 'BullEchipur 121' having orange colored flowers, good growth habit, more uniformity, good branching plant, and good propagation rates.

1 Drawing Sheet

Botanical classification: *Echinacea purpurea.*
Varietal denomination: 'BULLECHIPUR 121'.

BACKGROUND OF THE INVENTION

The present invention relates to a new and distinct cultivar of *Echinacea*, botanically known as *Echinacea purpurea*, and hereinafter referred to by the name 'BullEchipur 121'.

The new *Echinacea* was discovered by the Inventor in August 2021, in a controlled environment in Gönnebek, Germany, as a part of a planned breeding program. The new *Echinacea* was selected on the basis of orange colored flowers, good growth habit, more uniformity, good branching plant, and good propagation rates.

Asexual propagation of the new cultivar by in vitro culture since September 2021, in Gönnebek, Germany, has shown that the unique features of this new *Echinacea* are stable and reproduced true to type in successive generations.

SUMMARY OF THE INVENTION

The following traits have been repeatedly observed and are determined to be unique characteristics of 'BullEchipur 121'. These characteristics in combination distinguish 'BullEchipur 121' as a new and distinct cultivar:

1. Medium compact growths
2. Vibrant orange flowers
3. Lots of flowers
4. More branching habit
5. Very uniform growth
6. Nice green leaves
7. Fast crop time In side-by-side comparisons conducted by the Inventor in Gönnebek, Germany, plants of the new *Echinacea* differed from plants of the female parent, Bull 2019-17 of *Echinacea purpurea*, in the following characteristics:

1. More vigorous
2. Orange flower color

3. More branching
4. Bigger plant habit

In side-by-side comparisons conducted by the Inventor in Gönnebek, Germany, plants of the new *Echinacea* differed from plants of the male parent, Bull 2020-02 of *Echinacea purpurea*, in the following characteristics:

1. More compact
2. More intensive orange flower color
3. More branches
4. Lots of flowers Plants of the new *Echinacea* can be compared to the plants of the *Echinacea* cultivar 'Cheyenne Spirit' (a seedling selection from a breeding method described in U.S. Pat. No. 7,982,110), believed to be unpatented. In side-by-side comparisons conducted by the Inventor in Gönnebek, Germany, plants of the new *Echinacea* differed from plants of the cultivar 'Cheyenne Spirit' in the following characteristics:

1. More compact
2. Pure orange flowers
3. More flowers
4. More branching habit
5. Very even habit
6. Nice cleaner leaves with no necroses in or at the edges of the leaves, no brown spots in the middle of the leaves

DESCRIPTION OF THE DRAWINGS

The accompanying colored photographs illustrate the overall appearance of the new *Echinacea*, showing the colors as true as it is reasonably possible to obtain in colored reproductions of this type. Colors in the photographs may differ slightly from the color values cited in the detailed botanical description, which accurately describes the colors of the new *Echinacea*.

FIG. 1 comprises a top perspective view of a typical plant of 'BullEchipur 121' shown in natural lighting.

DESCRIPTION OF THE PLANT

The cultivar *Echinacea* has not been observed under all possible environmental conditions. The phenotype may vary somewhat with variations in environment such as temperature and light intensity without, however, any variance in genotype.

The aforementioned photographs and following observations and measurements describe plants of the new *Echinacea* that were grown in an outdoor nursery in Gönnebek, Germany. During the production of the plants, temperatures averaged about 18-20° C. Plants used for the photographs and description were about 22 weeks from planting. Color references are made to The Royal Horticultural Society Colour Chart, 2015 version, except where general terms of ordinary dictionary significance are used.

PLANT

Botanical classification: *Echinacea purpurea.*
Parentage: Bull 2019-17 and Bull 2020-02.
Propagation:

*Time to initiate roots.*—About 7 days.
*Time to develop roots.*—About 40-50 days.
*Time to produce a finished flowering plant.*—About 12-14 weeks.
*Root description.*—Lots of roots, free-branching, nice, healthy-looking root system.

Plant description:

*Growth rate/vigor.*—About 8 weeks to produce a young plant, and about 12 weeks from a potted young plant to a finished plant.
*Plant height.*—40-55 cm.
*Plant width.*—35-40 cm.
*Branching habit.*—Lot of branches, upright, shows a medium compact plant.
*Lateral branches.*—Number per plant: 20-25. Length: 2-35 cm. Diameter: 3-8 mm. Angle: 1-5 cm. Strength: Strong. Texture: Pubescent. Color: 146C. Internode length: 1-5 cm.
*Foliage.*—Stem Leaves: Length: 4-25 cm. Width: 1-7 cm. Shape: Lanceolate. Shape of Apex: Acuminate. Shape of Base: Attenuate to Acute. Orientation and aspect: Straight to curved. Texture: Upper surface: Rough. Lower surface: Rough. Young leaves: Upper surface color: 137A. Lower surface color: 137C. Fully expanded leaves: Upper surface color: 137A Lower surface color: 137C. Venation: Type: Cross-venulate to longitudinal. Color: Upper surface: 145A. Lower surface: 145B. Margin: Entire. Rugosity: Medium to strong. Basal Leaves: Length: Approximately 25 cm. Width: 1-7 cm. Shape: Lanceolate. Shape of Apex: Acuminate. Shape of Base: Attenuate to Acute. Orientation and aspect: Straight to curved. Texture: Upper surface: Rough. Lower surface: Rough. Young leaves: Upper surface color: 137A. Lower surface color: 137C. Fully expanded leaves: Upper surface color: 137A. Lower surface color: 137C. Venation: Type: Cross-venulate to longitudinal. Color: Upper surface: 145A. Lower surface: 145B. Margin: Entire. Rugosity: Medium to strong.

Flowers:

*Bud.*—Stage of opening: Single type blossom. Shape: Elliptic shaped ray florets and tubular disk florets. Diameter: 1-3.5 cm. Length: 1.2-2.5 cm. Color: N137C.
*Natural flowering season.*—13-14 weeks after planting.
*Inflorescence.*—Form: Single flower. Disc and ray floret arrangement: Single composite flower. Average number per plant: 20-30. Average number per branch: 1-3. Fragrance: None. Diameter: 4-10 cm. Height: 2-4.5 cm. Diameter of disc: 1.5-4 cm. Receptacle height: 1 cm. Receptacle diameter: 1.5-4 cm. Ray florets: Number per inflorescence: 16-24. Arrangement: In two or three whorls. Attitude: Horizontal to semi-drooping. Profile (in cross-section): Weakly convex. Length: 1.5-3.5 cm. Width: 0.9-1.5 cm. Shape: Ellipse. Shape of Apex: Mucronate to obtuse with very small notches. Shape of Base: Acute. Margin: Entire. Texture: Upper surface: Smooth, glabrous. Lower surface: Rough. Color: When opening: Upper surface: N30A. Lower surface: 35A. At maturity: Upper surface: N30A. Lower surface: 35A. Ground color description: Orange. Disc florets: Number per inflorescence: Numerous, too many to count. Arrangement: In center of receptacle, showing receptacle spine with a receptacle bracts. Average Height: 2.5-3.5 cm. Length: 8-15 mm. Width: 1-2 mm. Shape: Tubular. Shape of Apex: Sharp. Color: Immature: 181A. At maturity: 181A. Phyllaries: Number per inflorescence: 35-50.Arrangement: In 3-4 whorls. Length: 0.5-1.5 cm.

Width: 2-3 mm. Shape: Lanceolate. Shape of Apex: Elongate, oval. Shape of Base: Fused. Margin: Entire. Texture: Upper surface: Rough. Lower surface: Rough. Color: Immature: Upper surface: NN137C. Lower surface: NN137C. At maturity: Upper surface: NN137C. Lower surface: NN137C. Peduncle: Arrangement: Single stem. Color: 138C. Length: 7.0-11.0 cm. Texture: Haired and rough.

Reproductive organs:

*Androecium*.—Presence: On disk florets. Number: One. Filament: Length: 1-2 mm. Color: 183A. Anther: Shape: Oval. Length: 1 mm. Color: 183B. Pollen: Color: 15B. Amount: Too much to quantify.

*Gynoecium*.—Presence: In disk and ray florets. Pistil length: 1-2 mm. Stigma: Shape: Two-parted. Color: 183A. Style: Length: 1-2 mm. Color: 183A.

*Seeds/fruit*.—Length: 1-2 mm. Width: 2 mm. Color: Brown (165A).

Disease/pest resistance:

*Disease resistance*.—No additional disease resistance has been observed beyond the typical resistance in *Echinacea* plants.

*Pest resistance*.—No additional pest resistance has been observed beyond the typical resistance in *Echinacea* plants.

Weather tolerance:

*Temperature tolerance*.—No additional temperature resistance has been observed beyond the typical resistance in *Echinacea* plants.

*Drought tolerance*.—No additional drought resistance has been observed beyond the typical resistance in *Echinacea* plants.

I claim:

1. A new and distinct cultivar of *Echinacea* plant named 'BullEchipur 121', as herein illustrated and described.

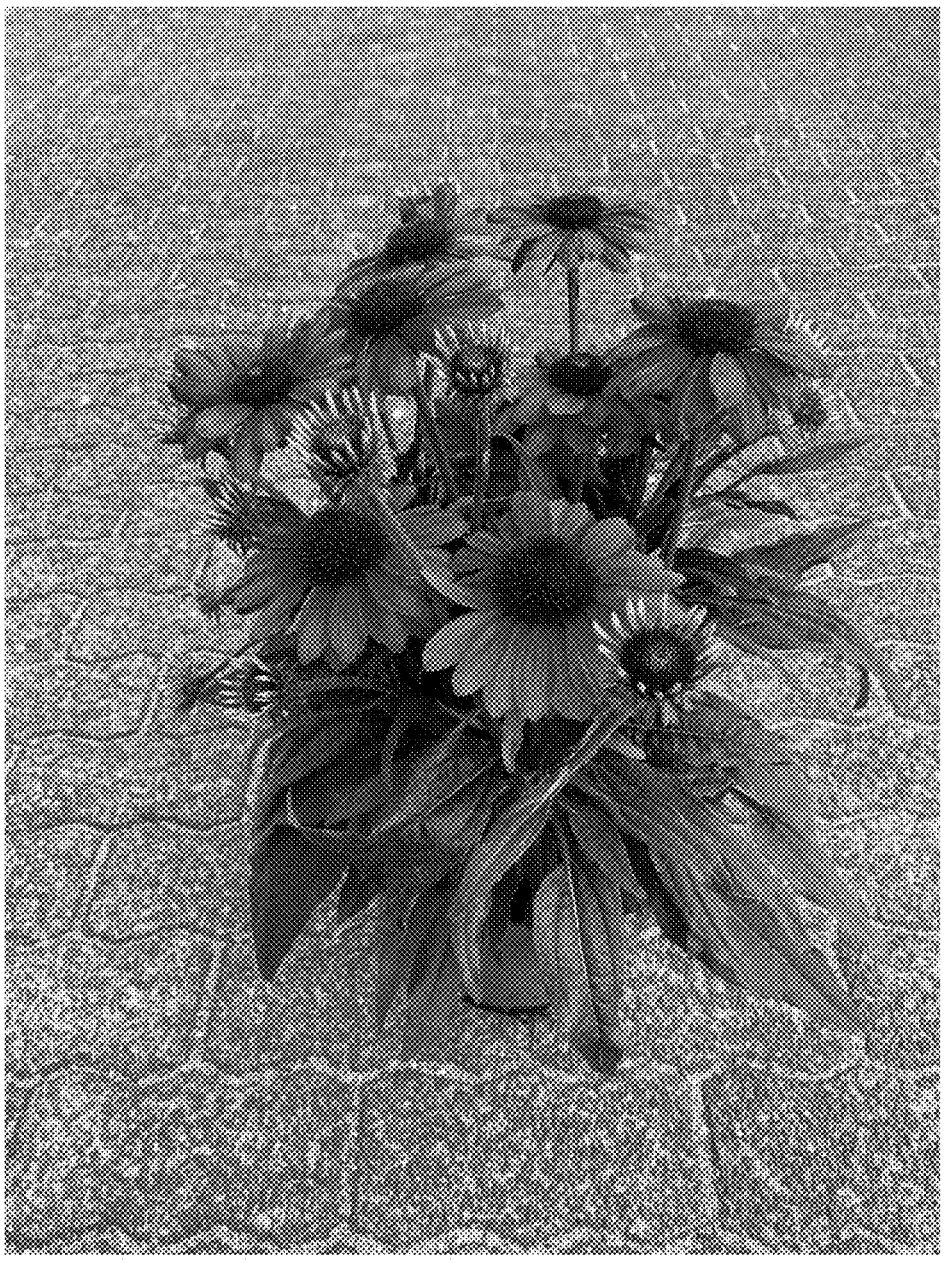

* * * * *